United States Patent [19]

Harris

[11] 4,059,512

[45] * Nov. 22, 1977

[54] PROCESS FOR REMOVING ENDOTOXIN FROM BIOLOGICAL FLUIDS

[75] Inventor: Nick S. Harris, Galveston, Tex.

[73] Assignee: Preventative Systems, Inc.

[ * ] Notice: The portion of the term of this patent subsequent to May 25, 1993, has been disclaimed.

[21] Appl. No.: 641,230

[22] Filed: Dec. 16, 1975

Related U.S. Application Data

[63] Continuation-in-part of Ser. No. 536,833, Dec. 27, 1974, Pat. No. 3,959,128.

[51] Int. Cl.$^2$ .............................................. B01D 15/00
[52] U.S. Cl. .................................. 210/24; 128/214 R; 128/DIG. 3; 210/DIG. 23; 424/78; 424/83; 424/101
[58] Field of Search ......... 128/214 B, 214 R, DIG. 3; 210/24, 500 M, DIG. 23; 424/78, 83, 101

[56] References Cited

U.S. PATENT DOCUMENTS

| | | | |
|---|---|---|---|
| 3,770,631 | 11/1973 | Fekete et al. | 424/101 |
| 3,794,584 | 2/1974 | Kunin | 210/24 |
| 3,959,128 | 5/1976 | Harris | 210/24 |

OTHER PUBLICATIONS

Nolan et al., "Effect of Cholestyramine on Endotoxin Toxicity and Absorption", *American Journal of Digestive Diseases*, vol. 17, No. 2, Feb. 1972, pp. 161–166.

*Primary Examiner*—Thomas G. Wyse
*Assistant Examiner*—Ivars Cintins
*Attorney, Agent, or Firm*—Pravel, Wilson & Gambrell

[57] ABSTRACT

A novel process for removing endotoxin from biological fluids such as parenteral fluids and for removing or reducing the level of endotoxin from the blood of animals is disclosed. The novel process includes the utilization of certain non-ionogenic hydrophobic synthetic plastic polymers that have been found to be capable of adsorbing endotoxin from the biological fluids when placed in intimate contact therewith.

3 Claims, No Drawings

PROCESS FOR REMOVING ENDOTOXIN FROM BIOLOGICAL FLUIDS

CROSS-REFERENCE TO RELATED APPLICATION

This application is a continuation-in-part of application Ser. No. 536,833, filed Dec. 27, 1974, now U.S. Pat. No. 3,959,128.

BACKGROUND OF THE INVENTION

This invention relates to the removal of endotoxin from biological fluids including the blood of animals and parenteral fluids, such as serum, plasma, whole blood, albumins, dextrose solutions, and the like. More particularly, the invention pertains to a novel process for removing endotoxin from such biological fluids through the use of certain nonionogenic hydrophobic synthetic plastic polymers or resins that are capable of adsorbing endotoxin present in the fluids.

Generally speaking, endotoxin is a complex lipopolysaccharide material derived from gram-negative bacilli that is known to produce a wide variety of striking pathophysiological reactions in aminals. Studies have demonstrated that endotoxin is distinguishable from classic protein toxins due to its failure to be neutralized by anti-serum, is increased heat stability and its failure to be converted to toxoid by treatment with formaldehyde. Moreover, endotoxin exhibits a lesser degree of potency than classic protein toxins and produces essentially similar reactions in animals regardless of the microbial orgin of the endotoxin. The material has been known and studied for many years particularly in regard to the pathophysiological reactions it causes in animals. For many years it was believed that the material was contained within gram-negative bacilli cells and was released only upon disintegration of the cell walls. Hence, the material was termed endotoxin. Recent studies, however, have shown that endotoxin is localized at the cell surface of gram-negative bacilli and may be present with viable and killed cells as well as in a free form within a liquid medium.

So far as is presently known, the complex lipopolysaccharide material commonly identified as endotoxin may be derived from all types of gram-negative bacilli including, by way of example, the Escherichia, Klebsiella, Proteus, Pseudomonas, Salmonella, Citrobacter, Bordetella, Serratia and Shigella types, to name a few. Endotoxins derived from different types of gram-negative bacilli are essentially the same in biochemical composition and structure and, as mentioned above, produce essentially similar reactions in animals.

As mentioned before, endotoxin is known to cause several striking and varied pathophysiological reactions and has been identified as a direct and contributory cause of death of many hospitalized patients. More particularly, endotoxin is known to cause febrile reactions in animals with symptons of extremely high fever, vasodilation, diarrhea, and the like and, in extreme cases, fatal shock. It is also known that endotoxin cause leucocytosis, deleterious changes in carbohydrate and protein metabolism and widespred intravascular clotting by fibrin formation.

Studies have shown that endotoxemia in animals may be caused by or is associated with gram-negative bacilli primary and secondary infections and/or the employment of intravenous apparatus or solutions contaminated with gram-negative bacilli or endotoxin. The occurrence of endotoxemia from the use of endotoxin-contaminated intravenous or parenteral solutions has recently been recognized as a particular problem in modern hospitals. In addition, it has recently been found that severe trauma, particularly trauma caused by thermal injuries, may cause the release of endotoxin from gram-negative bacilli of the noram flora of the gastrointestinal tract of animals. The studies have shown that there may be increased levels of endotoxin in the blood of traumatized animals even when the animals have no other diagnosed bacterial infection.

Under normal conditions the blood cells, i.e., leucocytes, of animals usually control the level of endotoxin in the blood. However, the blood cells usually cannot control excessive amounts of endotoxin of endotoxin experienced under abnormal conditions, such as those hereinabove mentioned, thereby resulting in endotoxemina. It is presently a common practice in the medical profession to counteract endotoxemia by treatment with massive infusions of antibiotics. However, it has not been shown that antibiotics remove endotoxin other than by controlling gram-negative bacilli. As mentioned hereinbefore, endotoxin is known to exist in free form in liquid media and may be associated with killed bacterial cells.

There are a few procedures known for removing or reducing the level of endotoxin in certain fluid media. For example, endotoxin may be removed from a liquid medium by filtration procedures employing macromolecular and/or activated carbon filters whereby the complex endotoxin molecules are filtered out. Osmotic pressure separation procedures have also been employed. These techniques have generally been employed in the purification of water and relativelysimple fluid compositions. However, such techniques have not been extensively used to remove endotoxin from biological fluids, particularly certain parenteral fluids, such as plasma, serum, albumins, whole blood and the like, apparently due to the extremely complex molecular and sometimes cellular composition of such fluids. In fact, it is common practice in the medical and pharmacological professions to merely destroy parenteral fluids contaminated with unacceptable levels of endotoxin.

I have now discovered a process for selectively removing endotoxin from substantially any biological fluid which does not otherwise adversely affect the molecular and/or cellular composition of the fluid. In fact, the process of my invention is particularly useful in removing and/or reducing the level of endotoxin in the blood of animals in accordance with in vivo hemoperfusion techniques. The inventive process is based upon the surprising discovery that certain non-ionogenic hydrophobic synthetic plastic polymers have specific affinity for endotoxin when placed in intimate contact therewith.

Several types of synthetic plastic resins or polymers have heretofore been used in various processes for treating parenteral fluids and/or blood. For example, there are several known procedures for treating parenteral fluids by the employment of ion-exchange resins. More particularly, ion-exchange resins have been employed in processes for treating parenteral fluids, including blood, with anionic and cationic agents, for separating certain protenatious materials from blood, for preparing sterile parenteral fluids difficult to sterilize, such as bicarbonate ion solutions, and the like. See U.S. Pat. Nos. 3,769,401; 3,097,141; 3,234,199; 2,682,268; and 3,305,446 to name a few. The ion-exchange resins employed in these processes are basically comprised of monomers and/or polymers of styrene or vinyl benzene treated with many types of polyelectrolytes.

It is known that certain types of strong basic anion exchange resins have an affinity for bacterial endotoxin. James B. Nolan and M. Vilawat Ali, in "Effect Of Cholestyramine On Ednotoxin Toxicity And Absorption", *American Journal Of Digestive Diseases,* Vol. 17, No. 2 (February, 1972), have reported that the addition of cholestyramine or DOWEX 1-X8 (Dow Chemical Company), both strong basic anion exchange resins, to an endotoxin mixture impedes its absorption in the isolated gut sac, and reduces its toxicity when injected intraperitonially. However, it has not been reported that the described ion-exchange resins are capable of selectively absorbing and removing bacterial endotoxin from complex biological fluids, such as albumin, blood, etc. As known, such ion-exchange resins are strongly ionogenic and, thus, may adversely affect such complex biological fluids. Furthermore, such resins are completely different types of resins, chemically, physically, etc., from the certain types of non-ionogenic hydrophobic synthetic plastic polymers described below which I have found to have specific affinity for bacterial endotoxin when placed in intimate contact therewith.

U.S. Pat. No. 3,794,584 teaches a process for removing poisonous or toxic amounts of barbiturates and glutethimides from blood which includes perfusing blood over a column of an essentially non-ionogenic macroreticular watersoluble cross-linked polymer having a porosity of at least 10% and a specific surface area of at least 10 square meters per gram. The polymer resin employed is described as being comprised of from 2 to 100 weight percent of a poly(vinyl)benzene monomer polymerized with one or more mono- or polyethylinically unsaturated monomers. The disclosed poly(vinyl)-benzene-based macroreticular polymer resins are described as being capable of adsorbing the barbiturates and glutethimides from the blood without otherwise adversely affecting the blood.

U.S. Pat. No. 3,706,661 teaches a method for the separation of biological cells from solutes by use of macroporous synthetic plastic resin gels, particularly gels of polyacrylamide and hydrophilic polymethacrylates. U.S. Pat. No. 3,839,314 describes a process of clarifying blood serum and plasma to remove undesired protenatious and lipid matter by the employment of block copolymers of ethylene oxide and a polyoxypropylene polymer. There are also several prior art references which describe the use of certain synthetic plastic resins, such as nylon, acrylonitrile polymers, polyesters, and polytetrafluoroethylene in fiber or textile form as filter media to remove materials from certain parenteral fluids. See U.S. Pat. Nos. 3,462,361; 3,448,041; 3,036,575; 3,533,400; and 2,702,036.

However, to my knowledge, the synthetic polymeric resins that I have found to be capable of adsorbing endotoxin have not heretofore been specifically employed in any prior art processes for treating biological fluids, particularly for removing endotoxin. Furthermore, many types of synthetic resins heretofore employed in processes for treating biological fluids to remove certain components have been found to have no affinity for endotoxin.

SUMMARY OF THE INVENTION.

The present invention is a novel process for removing endotoxin from biological fluids such as parenteral fluids and for removing or reducing the level of endotoxin from the blood of animals which comprises intimately contacting a biological fluid contaminated with endotoxin with a non-ionogenic hydrophobic non-polar aliphatic synthetic polymer or resin capable of adsorbing endotoxin which may be selected from the group consisting of substantially crystalline non-polar aliphatic hydrocarbon thermoplastic polymers, fluorocarbon polymers, silicone elastomeric polymers, and mixtures thereof. The biological fluid may then be removed from intimate contact with the polymer or resin essentially free of endotoxin. The endotoxin remains tightly bound to the polymer material. The invention represents a tremendous advance in the art for it provides a process for directly and selectively removing endotoxin from substantially any type of biological fluid, even those of highly complex composition. Moreover, the process of the invention can be employed in an in vivo hemoperfusion process to remove and/or reduce the level of endotoxin in the blood of animals.

DETAILED DESCRIPTION OF THE INVENTION

In accordance with the present invention, synthetic plastic polymers or resins that have been found to be capable of adsorbing exdotoxin are normally hydrophobic, non-ionogenic and substantially non-polar. These polymers are also aliphatic materials. More particularly, types of synthetic plastic polymers that have been found capable of adsorbing endotoxin include substantially crystalline, non-polar aliphatic hydrocarbon thermoplastic polymers, fluorocarbon polymers, silicone elastomers and mixtures thereof. The mechanism whereby these type of synthetic plastic polymers adsorb endotoxin is not understood. Experiments have shown that when a biological fluid contaminated with endotoxin is contacted with these types of polymers the endotoxin is readily removed from the liquid media. These experiments have further shown that the endotoxin removed is tightly bound to the synthetic polymer surface and is not readily removed by simple washing. Yet, many types of synthetic polymer or resin materials heretofore employed for removing certain types of compounds from biological fluids have been found to be incapable of adsorbing endotoxin. Examples of some of these materials include polystyrene, nylon (polyamide), poly(methylmethacrylate), and polycarbonate, to name a few.

These synthetic polymer materials that have been found to be incapable of adsorbing endotoxin are, generally, amorphous, atactic polymers. Many of these polymers also contain aromatic groups and/or are ethylenically unsaturated. Conversely, as mentioned hereinbefore, the types of polymers that have been discovered to have an affinity for and are capable of adsorbing endotoxin are generally aliphatic polymers which are non-ionogenic, substantially non-polar and hydrophobic. Moreover, many of these polymers are classified as crystalline, isotactic polymers.

The substantially crystalline non-polar aliphatic hydrocarbon thermoplastic polymers preferably employed in the process of the invention include the poly-α-olefins, such as polyethylene, polypropylene, and the higher homologue polymers. Any commercially available type or grade of poly-α-olefin may be employed in substantially any molecular weight commercial formulation. The polymers may include inert compatible fillers and/or colorants with no adverse affect on their capability of adsorbing endotoxin. Moreover, copolymers may be employed. Examples of particular commercially available poly-α-olefins that have been found useful include high density polyethylene, low density polyethylene, and isotactic piolypropylene, to name a few.

Fluorocarbon polymers have also been found to have an affinity for endotoxin and are extremely useful in the process of the invention. As known, fluorocarbon polymers are highly crystalline, hydrophobic, non-ionogenic and substantially non-polar thermoplastics. Any commercially available fluorocarbon polymer material may be employed in the inventive process, including those substituted with other halogens, such as chlorine, and those formulated with inert fillers or colorant ingredients. Types of fluorocarbon polymers that have been found to be particularly useful include tetrafluoroethylene polymers, fluorinated ethylenepropylene polymers and modified copolymers of tetrafluoroethylene and ethylene. These polymers are readily available commercially in a variety of grades. For example, fluorinated ethylene-propylene polymers are sold by E. I. du Pont de Nemours & Co., Inc. under the trademark TEFLON FEP. Modified copolymers of tetrafluoroethylene and ethylene are also sold by E. I. du Pont de Nemours & Co., Inc. under the trademark TEFZEL.

Furthermore, any type of silicone elastomer may be employed in the process of the invention. Silicone elastomers are classified as thermosetting cross-linked synthetic polymers and are normally quite resilient. Thus, their physical characteristics are somwhat different from the crystalline non-polar aliphatic hydrocarbon polymers and fluorocarbon polymers mentined hereinabove. Yet, experiments have shown that silicone elastomers have an affinity for endotoxin and are capable of adsorbing it from a liquid medium. Types of silicone elastomers that are particularly useful in the process of the invention include the high molecular weight linear poly (alkylsiloxane)s that are cured by cross-lining linear or slightly branched siloxane chains having reactive silanol end groups. These silicone elastomers are generally referred to in the art as room-temperature vulcanizing silicone elastomers and are readily available commerically. Any of these commercially available materials may be employed, including those containing inert filler and/or colorant ingredients. Examples of suitable silicone elastomers include the RTV 732 and 108 silicone elastomers sold by Dow Corning Company, which contain dimethyldichlorosilane and cross-linking agents that cure by cross-linking when exposed to atmospheric moisture. Another suitable silicone elastomer is medical grade silastic sold by Dow Corning Company which is cross-linked and cured at room-temperature by the addition of stannous octoate. These silicone elastomers are employed in the process of the invention after they have been cured or cross-linked to form solidified materials which are then particulated.

In carrying out the process of the invention, the above non-ionogenic hydrophobic synthetic polymers or resins may be employed in essentially any desired physical form or structure. Preferably they are utilized in particulate form, such as granules, beads, irregular chips, fibrous strands and the like so as to provide increased exposed surface area per volume or weight. Additionally, these polymers may be employed in the form of one or more continuous porous layers, e.g., as porous sheets, membranes or films, such as non-woven webs, woven sheets, microporous films, etc., with substantially similar and oftentimes superior results being observed, as described more particularly below.

The particulate size and volume of polymer employed in particulated form has not been found to be particularly critical. However, it is preferred to employ substantially spherical beads or granules of the polymer when highly complex fluids containing biological cells are treated so as to prevent damage and/or agglomeration of cells, particularly blood cells. Moreover, it is preferred to employ the particulated synthetic polymer or resin in a volume excess of that required to remove substantially all endotoxin from a contaminated biological fluid. The volume of polymer or resin employed is variable, depending upon the degree of endotoxin contamination, polymer particulate size, and volume of fluid to be treated. The particular volume of polymer or resin employed for treating a given sample of a biological fluid is best determined empirically and may be readily determined by one having ordinary skill in the art without undue experimentation. It is particularly preferred to employ losely packed columns of polymer beads or granules having a diameter of about 0.5 mm to about 4 mm.

Similarly, where porous sheets or films of the above polymers are employed, the specific pore size, porosity, film thickness, density, etc. are not particularly critical. However, the porous sheet, film or membrane employed preferably has a sufficient effective pore size to prevent the trapping or filtering of desirable molecular and/or cellular components from the biological fluid treated.

There are many types of porous sheets, films and membranes manufactured from several of the above-described polymers, especially the poly-α-olefins, which are commercially available and have been found suitable for use in the practice of the present invention. Examples of some of these commercially available materials include non-woven webs, woven sheets and microporous films or membranes of polyethylene, polypropylene and copolymers thereof. As known, these materials have a wide range of effective pore sizes, porosities, thicknesses, etc., depending upon the process employed in their manufacture.

The particular type of porous sheet, film or membrane which may be employed in accordance with the process of the invention to remove endotoxin from a given biological fluid may be readily determined by one having ordinary skill in the art without undue experimentation. Technical data on the properties of these films are readily available from the manufacturers. Moreover, the chemical and/or cellular compositions of most biological fluids have been documented in the literature. As demonstrated in one of the following examples, porous membranes of the above polymers employed in accordance with the inventive process do not remove endotoxin from a biological fluid by physical filtration. Hence, the particular porous membrane employed in the process of the invention preferably has pores of sufficient size to permit the biological fluid being treated to be passed through without removal of desired chemical and/or cellular components therefrom.

By way of specific example, microporous films of polyethylene and polypropylene manufactured and sold by Celanese Plastics Company under the trademark CELGARD have been found to be particularly effective in removing endotoxin from biological fluids in accordance with the inventive process. These microporous hydrophobic homopolymer films are available with effective pore sizes of from about 0.02 to about 0.50 micrometers, porosities of from about 38 to about 65% and have nominal thicknesses of about 1 to about 4 mils.

Further, in carrying out the process of the invention the biological fluid contaminated or suspected to be contaminated with endotoxin is preferably passed or perfused through a column containing the above-described particulated or continuous porous layer of synthetic polymer or resin at a volume flow rate sufficient to provide an intimate contact of endotoxin present with the polymer surface. Where the polymers are utilized in continuous porous layer or filler form, it is especially preferred to pass or perfuse the biological fluid completely therethrough. A gravitational flow rate has been found to be usually sufficient. However, if desired, a slight positive pressure may be employed to increase the fluid flow rate. In addition, it is preferred to slightly agitate the column of polymer material as the biological fluid is passed through so as to enhance contact of the endotoxin with the polymer surface and increase the fluid flow rate. Slight agitation is particularly helpful when the biological fluid being treated contains biological cells, such as whole blood, to reduce agglomeration of the cells.

As mentioned hereinbefore, the process of the invention may be employed to effectively remove endotoxin from substantially any type of biological fluid including parenteral fluids and may also be employed in an in vivo hemoperfusion technique to remove and/or reduce the level of endotoxin in the blood animals. Examples of parenteral fluids that may be treated by the process include saline solutions, dextrose solutions, hyperalimentation fluids, serums, plasma, albumins, whole blood, and antiserums, to name a few. When treating such parenteral fluids by the process of the invention, it is preferred to pass the parenteral fluid by gravitational flow or under slight positive pressure and through a column containing the particulated synthetic polymer or resin or the porous polymer or resin membrane, etc., as described above. The parenteral fluid may be treated immediately before use so as to reduce the possibility of later contamination.

In a preferred embodiment the process of the invention may be employed for removing and/or reducing the level of endotoxin in the blood of an animal by an in vivo hemoperfusion polymer-column technique. More particularly, in this preferred embodiment, heparinized blood from an animal is removed through an arterial by-pass and perfused through a column or housing containing granules or beads, or at least one porous sheet or membrane, of one or more of the above-described synthetic polymers capable of removing endotoxin. When polymer beads or granules are employed, they preferably have an average particle size of from about 0.5 mm to about 4.0 mm diameter. Additionally, the polymer beads or granules are preferably employed in an amount of about 50 to about 250 g. per kilogram weight of the animal. Similarly, when the porous polymer sheet or membrane is employed, it has an effective pore size sufficiently large to permit the passage of blood cells therethrough and to provide adequate blood flow rates.

After the blood has been perfused through the polymercolumn, it is then reinfused into the animal. Preferably, during perfusion of the polymer-column is slightly agitated to reduce the possibility of agglomeration and/or filtration of blood cells.

The process may be continued as long as desirable and has been found to effectively remove and control the level of endotoxin in the blood of the animal as shown by some of the examples set forth hereafter. Moreover, it has been found that the process does not adversely affect the blood composition.

The following examples particularly illustrate the nature of the inventive process but are not intended to be limitative thereof. In the following examples, the presence and amount of endotoxin present were determined by the use of the Limulus Lysate Assay, which is an assay based on the gelation of amebocyte lysate from *Limulus polyphemus*, the horseshoe crab. The Limulus Lysate Assay has been described as the most sensitive method presently available for the detection of endotoxin. See R.R. Rojas-Corona, et al. "The Limulus Coagulation Test for Endotoxin: A Comparison With Other Assay Methods", Proceedings of the Society for Experimental Biology and Medicine 132, 599-601 (1969); and James H. Jorgensen et al. "Measurement Of Bound And Free Endotoxin By The Limulus Assay", Proceedings of the Society for Experimental Biology and Medicine 146, 1024–1031 (1974). The assay is performed by incubating a sample of a fluid suspected of containing endotoxin with an equal volume of the amebocyte lysate from the horseshoe crab, *Limulus polyphemus*. The degree and quality of gelation observed is directly related to the amount of endotoxin present. The assay has been found to be so sensitive so as to detect as little as 0.1 nanogram of endotoxin.

Except as noted, the Limulus lysate employed in the following examples for the respective assays was prepared in accordance with a known published procedure for lysing amebocytes of the hemolymph of Limulus crabs. The crabs were obtained from the Marine Biological Laboratory, Woods Hole, Mass. The amebocyte cells were lysed by the addition of pyrogen-free distilled water at a 1:3 ratio of packed cells to water. The suspension was then thoroughly mixed and allowed to stand at 4° C. for 18–24 hours. The cellular debris was then removed by centrifugation and the lysate decanted. The lysate was stored in sterile pyrogen-free polystyrene vials at −20° C., or for shorter periods of time at 4° C., until needed.

EXAMPLE I

An endotoxin standard was prepared by adding 10 mg endotoxin to 10 ml pyrogen-free saline (0.9% sodium chloride) to yield a solution of 1 mg/ml concentration. The endotoxin used was a lipopolysaccaride Westphal phenol extract of *Escherichia coli* 011:B4, sold by Difco Laboraories, Detroit, Michigan. This initial 1 mg/ml endotoxin concentration solution was then diluted several times with pyrogen-free saline using dilution factors of 1:10 to provide several samples having endotoxin concentrations of 100 ng/ml, 10 ng/ml, and 1 ng/ml. A sample having an endotoxin concentration of 0.5 ng/ml was also prepared. These endotoxin standard solutions were prepared in polystyrene test tubes sold by Falcon Plastics, Oxnard, California. A 1.0 ml sample of the endotoxin solution having a concentration of 100 ng/ml was then added to a polystyrene test tube (Falcon Plastics, supra) containing 2 cc of raw polypropylene beads, about 2 mm average diameter, (Shell Polypropylene 5520, Shell Chemical Company, Houston, Texas) and held for 10 minutes at room-temperature with gentle shaking every three minutes. 0.1 cc of this sample as well as 0.1 cc from several other samples of the endotoxin standard solution were then collected for assay. The assay was conducted by adding the 0.1 cc samples to 0.1 cc, respectively, of Limulus lysate. Each sample assayed was incubated with the lysate for 70 minutes at 37° C. The resultant reactions were observed and graded for degree and quality of gelation as follows:

+4 Firm clot and cloudy.
+3 Soft clot which slides down inverted tube, cloudy.
+2 High viscosity slime and cloudy.
+1 Medium viscosity and maybe cloudy.
0 substantially clear, like water.

The results of the assay of the samples are set forth in the following Table 1.

TABLE 1

| Tube | Content | Concentration ng/ml | Reaction |
|---|---|---|---|
| 1 | Saline (control) | 0 | 0 |
| 2 | Endotoxin standard | 100 | +4 |
| 3 | Endotoxin standard | 10 | +4 |
| 4 | Endotoxin standard | 1 | +3 |
| 5 | Endotoxin standard | .5 | +2 |
| 6 | Treated Endotoxin standard | 100 | +2 |

As the results of Table 1 show, the polypropylene beads effectively removed over 995 of the endotoxin present in the treated sample, Tube 6. This 100 ng/ml endotoxin concentration sample should have given a +4 reaction, as Tube 2. However, surprisingly, it reacted substantially similar to the 0.5 ng/ml endotoxin standard sample analyzed.

EXAMPLE II

Two 12 cc syringes were respectively filled with 10 cc of two types of raw polypropylene beads (Shell Polypropylene 5520 and Shell Polypropylene 5820, Shell Chemical Company, supra). A third 12 cc syringe was filled with 10 cc of nylon fibers obtained from a Fenwal Leucopack filter (Baxter Laboratories, Inc., Chicago, Illinois). A fourth 12 cc syringe was filled with 10 cc of polystyrene chips prepared by particulating polystyrene rest tubes (Falcon Plastics, supra) into approximately 8 mm × 2 mm × 6 mm chips. To each syringe was added 3.0 cc of the endotoxin standarized solution prepared in Example I at a concentration of 100 ng/ml endotoxin. The endotoxin standard solutions passed through the respective polymer columns by gravitational flow and were collected for assay. The treated solutions were then assayed utilizing the Limulus Lysate Assay as described in Example I along with several endotoxin standard solutions at various concentrations for comparison. The results of the assays are set forth in the following Table 2.

TABLE 2

| Sample No | Material | Concentration[1] ng/ml | Reaction |
|---|---|---|---|
| 1 | Endotoxin Standard | 100 | +4 |
| 2 | Endotoxin Standard | 10 | +4 |
| 3 | Endotoxin Standard | 5 | +4 |
| 4 | Polypropylene[2] | 100 | +3 |
| 5 | Polypropylene[3] | 100 | +2 |
| 6 | Nylon | 100 | +4 |
| 7 | Polystyrene | 100 | +4 |

[1]Endotoxin concentration. Original concentration of solutions before treatment.
[2]Shell Polypropylene 5520, Shell Chemical Company.
[3]Shell Polypropylene 5820, Shell Chemical Company.

A comparison of the assay reaction results of Table 2 illustrate that the treatment of the endotoxin solutions in accordance with the present invention utilizing polypropylene beads resulted in removal of endotoxin from the solutions to a level of below 5 ng/ml. The results of Table 2 also show that nylon and polystyrene were ineffective in removing the endotoxin from the test solutions.

EXAMPLE III

In this example several experiments were conducted to determine the capability of various types of synthetic polymers or resins for removing endotoxin from a saline solution, employing the procedures described in Example I. Several endotoxin standard solutions were freshly prepared by initially adding 10 mg endotoxin (Westphal phenol extract of *Escherichia coli* 011:B4, Difco Laboratores, supra) to 10 ml pyrogen-free saline (0.9% sodium chloride). The resulting solution of 1 mg/ml endotoxin concentration was then diluted several times with the pyrogen-free saline to get several samples having final concentrations of 100 ng/ml, 10 ng/ml, 5 ng/ml, 2.5 ng/ml and 1 ng/ml endotoxin. The endotoxin solutions were then mixed with Limulus lysate for standardization employing the Limulus Lysate Assay procedure described in Example I which resulted in the following reactions:

| Endotoxin Solution-Lysate Standardization | |
|---|---|
| Endotoxin Concentration | Limulus Lysate Assay Reaction |
| 0 (saline control) | 0 |
| 100 ng/ml | +4 |
| 10 ng/ml | +4 |
| 5 ng/ml | +4 |
| 2.5 ng/ml | +3 |
| 1 ng/ml | +1 to +2 |

1 ml aliquots of three standardized endotoxin solutions having concentrations of 100 ng/ml, 10 ng/ml and 1 ng/ml, respectively, were then added to various types of particulated synthetic polymer or resin materials in the form of beads or chips having average particle sizes of about 2 mm in 10 cc polystyrene tubes (Falcon Plastics, supra) and allowed to sit at room-temperature for 10 minutes. 0.1 ml of each solution sample was then removed and assayed using the Limulus Lysate Assay procedure described in Example I. The types of synthetic polymers and amounts tested and Limulus Lysate Assay reaction results of each solution at each concentration are set forth in the following Table 3.

TABLE 3

| Synthetic Polymer | Particle form | Weight, grams | Lysate Assay Reaction | | |
|---|---|---|---|---|---|
| | | | 100 ng/ml | 10 ng/ml | 1 ng/ml |
| Polypropylene | beads | 2.4 | +3 | +2 | +1 |
| Polyethylene[2] | beads | 5.9 | +2 | +1 | +1 |
| Spun glass | fibers | .5 | +4 | +4 | +1 |
| Poly(methylmethacrylate) | chips | 5.0 | +4 | +4 | +1 |
| Silicone Elastomer[3] | chips | 3.8 | +3 | +1 | +1 |
| Silicone Elastomer[4] | chips | 3.7 | +4 | +2 | +1 |
| Silicone Elastomer[5] | chips | 3.9 | +1 | +1 | +1 |

[2]Alathon 7040 high density polyethylene, E. I. du Pont de Nemours & Co., Inc.
[3]RTV 732 dimethyldichlorosilane; Dow Corning Co. Elastomer was room-temperature vulcanized by exposure to atmosphere for 48 hours and cut into chips, about 2 mm diameter, prior to use.
[4]RTV 108 dimethyldichlorosilane; Dow Corning Co. Also room-temperature vulcanized and cut into chips prior to use as (3).
[5]SIL 382 medical grade silastic cross-linked and cured by addition of stannous octoate; Dow Corning Co. After 48 hours, cut into chips prior to use.

A comparison of the results of the above Table 3 with the endotoxin solution Lysate standardization of this Example demonstrates the ability of poly-α-olefins and silicone elastomers to adsorb endotoxin even when merely placed in intimate contact with the endotoxin contaminated solutions. Of the endotoxin standardized solutions employed in this Example, these materials effectively lowered the concentration of endotoxin to below about 2.5 ng/ml. The results of Table 3 also illustrate that spun glass fibers, and poly(methylmethacrylate) chips, conventionally used parenteral fluid filter materials, do not readily adsorb or exhibit an affinity for endotoxin.

EXAMPLE IV

In this example five types of synthetic polymer materials were employed to determine their capability of adsorbing endotoxin when employed in accordance with the process of the invention. The synthetic polymers employed were: polypropylene beads (Shell Polypropylene 5820, supra; polyethylene beads (Alathon 7040 high density polyethylene, supra); TEFLON FEP 100 fluorinated ethylene-propylene polymer (E. I. du Pont de Nemours & Co., Inc.); TEFZEL 200 modified copolymer of ethylene and tetrafluoroethylene (E. I. du Pont de Nemours & Co., Inc.); and polypropylene staple fiber (Hercules, Inc.). All of these polymer materials were washed with pyrogen-free distilled water. The polymer beads had an average size of about 2 mm. The polypropylene staple was also washed in a 70% solution of ethanol, pyrogen-free saline and then pyrogen-free distilled water. Each of the polymer materials were then respectively placed in 12 cc syringes to the 12 cc level. 1 cc aliquots of the endotoxin solution prepared and standardized as described in Example III, having an endotoxin concentration of 50 ng/ml, were then perfused through the syringes by gravitational flow. 0.1 cc of each treated solution was then added to 0.1 cc of the Limulus lysate, incubated at 37° C. for 70 minutes and the resultant reaction was observed and graded for degree and quality of gelation. The results are set forth in the following Table 4.

TABLE 4

| Synthetic Polymer | Endotoxin Concentration ng/ml[1] | Lysate Assay Reaction |
| --- | --- | --- |
| Endotoxin Control | 50 | +4 |
| Endotoxin Control | 10 | +4 |
| Endotoxin Control | 5 | +4 |
| Endotoxin Control | 2.5 | +3 |
| Endotoxin Control | 1 | +1 to +2 |
| Polypropylene | 50 | +3 |
| Polyethylene | 50 | +3 |
| TEFLON FEP 100 | 50 | +2 |
| TEFZEL 200 | 50 | +2 |
| Polypropylene staple | 50 | +3 |

[1]Endotoxin concentration prior to treatment.

The results of Table 4 illustrate the capability of fluorocarbon polymers for adsorbing endotoxin. The results of this table also demonstrate the affinity of polypropylene to endotoxin in various particulate forms and confirm the results obtained with regard to polypropylene and polyethylene in the previous examples.

EXAMPLE V 100 ng of endotoxin (lipopolysaccharide Westphal phenol extract, *E. coli* 011:B4, Difco, supra) was seeded in 1.0 ml normal human serum albumin, USP 25% salt poor, (sold under the tradename METALBUMEN by Metabolic, Inc., Houston, Texas) in a pyrogen-free polystyrene tube. A 1.0 ml sample of the albumin was also added to a second pyrogen-free polystyrene tube. Two polypropylene beads (Shell Polypropylene 5820, supra), having diameters of about 2 mm, were respectively placed in each of the tubes. The samples were incubated at 37° C. for 10 minutes. The two beads were then removed, washed with pyrogen-free saline, and assayed for the presence of endotoxin by adding each bead to 0.1 ml Limulus lysate, incubating at 37° C. for 70 minutes and grading the resultant reaction for degree and quality of gelation in accordance with the Limulus Lysate Assay procedure described in Example I. Several endotoxin solutions at various concentrations were prepared by dilution of the endotoxin in saline, as described in Example I. 0.1 ml of the prepared endotoxin solution, along with a 0.1 ml sample of the albumin were also assayed by the Limulus Lysate Assay as controls. The results of the assays are set forth in the following Table 5.

TABLE 5

| Material Assayed | Endotoxin Concentration, ng/ml | Limulus Lysate Assay Reaction |
| --- | --- | --- |
| Endotoxin Control | 100 | +4 |
| Endotoxin Control | 10 | +4 |
| Endotoxin Control | 1 | +2 |
| Albumin Control | — | +1 |
| Polypropylene bead[1] | 100 | +4 |
| Polypropylene bead[2] | — | 0 |

[1]Bead placed in 1 ml albumin seeded with 100 ng endotoxin, incubation at 37° C. for 10 minutes. Bead washed with saline prior to assay.
[2]Bead placed in 1 ml albumin control, incubation at 37° C. for 10 minutes. Bead washed with saline prior to assay.

The results of Table 5 illustrate the endotoxin present in albumin was adsorbed by polypropylene and the adsorbed endotoxin was tightly bound to the polypropylene bead surface. The polypropylene bead contacted with the endotoxin seeded albumin gave a strong +4 assay reaction even after being washed with pyrogen-free saline.

EXAMPLE VI

A hemoperfusion polymer-column apparatus was designed to perform an arterial-venous shunt or bypass to determine the effectiveness of the inventive process for removing and/or reducing the level of endotoxin in the blood of an animal in vivo. The hemoperfusion polymer-column unit was prepared by packing a sephadex gel reservoir, 5 mm diameter, 30 cm long, with 800 g. of polyethylene beads having diameters of about 2 mm, average, (ALATHON 7040 high density polyethylene, Du Pont, supra). Intravenous tubes were attached to each end of the reservoir and capped with catheters. The apparatus was then attached to a dog, weighing 12 kilograms, by injecting one catheter into an artery and the other catheter into a vein. The dog had previously been heparinized by injection with sigma pyrogen-free heparin at a dose level of about 6 units per cc of blood (approximate dose, 6000 units heparin). The blood from the animal was removed through the arterial intravenous line, perfused through and over the polyethylene bead column and reinfused through the venous intravenous line. The column containing the polyethylene beads was gently shaken by the use of a reciprocal shaker to prevent agglomeration of blood cells. After 1 hour of continuous perfusion no hemolysis was observed. The dog was then intravenously injected with 5 mg/kg weight endotoxin (lipopolysaccharide Westphal phenol extract of *E. coli*, 055:B5, Difco Laboratories, supra; reconstituted with pyrogen-free saline, 0.9% sodium chloride). This level of endotoxin injection is generally referred to as a LD-80 dose, which is an amount sufficient to be fatal to 80% of dogs injected within a 6 hour period. After injection the dog's vital signs were continously monitored. During this time the dog developed hypotension, hypoxia, metabolic acidosis, hypocapnia, and tachypnia. The arterial-venous bypass through the hemoperfusion polymer-column apparatus was continued for 1.5 hours after the endotoxin injection and then the apparatus was removed. 3 hours after the endotoxin injection, the dog was observed as to be resting comfortably with normal signs. Observation was continued for 24 hours after which the mentioned symptoms of acute endotoxemia no longer appeared.

EXAMPLE VII

In this example, a hemoperfusion apparatus was prepared in accordance with the design described in Example VI, except that the ends of the sephadex gel reservoir were covered with cotton gauze to prevent clogging and 800 g. of polypropylene beads, having average sizes of about 2 mm, were placed in the reservoir (Shell Polypropylene 5820, supra). This hemoperfusion polymer-column apparatus was attached to a dog weighing 17 kg as described in Example VI. After about 1 hour of continuous bypass of the blood perfused through the polymer-column no hemolysis was observed. The dog was then injected with 5 mg/kg weight of the endotoxin and perfusion of the blood through the polymer-column was continued for 1½ hours thereafter. A few minutes after the endotoxin injection the animal developed the symptoms of acute endotoxemia described in Example VI. The arteria-venous shunt was then discontinued by removal of the hemoperfusion apparatus. The polypropylene bead in the reservoir were then washed by perfusing pyrogen-free saline through the polymer-column. One of the beads was removed and added to 0.1 cc saline. 0.1 cc of the Limulus lysate was then added thereto and incubated at 37° C. for 70 minutes. During the incubation, a clot appeared.

The results of Examples VI and VII demonstrate the effectiveness of the process of the invention for removing and/or reducing the level of endotoxin in the blood of animals when employed in an in vivo hemoperfusion or arterial-venous by-pass technique whereby blood from the animal is removed, perfused through a column of the polymer capable of adsorbing endotoxin and then the blood is reinfused into the animal. Moreover, Example VII confirms that endotoxin in the blood of the animals is tightly bound to the bead surfaces as demonstrated in Example V.

EXAMPLE VIII

Several endotoxin standard solutions were prepared by adding 10 mg Salmonella endotoxin (Westphal phenol extract of *Salmonella typhosa* dispersed in pyrogen-free saline, #612016, lot #0901, Difco Laboratories, supra, to 10 ml sterile (pyrogen-free) distilled water. The resulting solution of 1 mg/ml endotoxin concentrate was then successively diluted several times with the sterile water to provide several standards having final concentrations of 10 ng/ml, 5 ng/ml, and 1 ng/ml endotoxin.

A sterile 12 cc syringe was filled with polypropylene beads (Shell Polypropylene 5820, supra) having average bead sizes of about 2 mm. The beads had been previously washed with successive washes of sterile distilled water, a 70% solution of ethanol and pyrogen-free saline and sterile distilled water. 10 ml of the 1 ng/ml endotoxin standard was perfused through the polymer-containing syringe. Additionally, two of the previously washed beads were respectively placed in a test tube containing 10 ml of the 10 ng/ml endotoxin standard and a test tube containing the distilled water and respectively incubated for 30 minutes at 37° C. The beads were then removed from the test tubes, washed with sterile distilled water, added to 0.2 cc and 0.1 cc, respectively, of Limulus lysate and incubated at 37° C. for 90 minutes. Similarly, 0.1 cc aliquots of each of the endotoxin standards and the standard passed through the polymer-containing syringe were added to 0.1 cc aliquots of Limulus lysate and incubated at 37° C. for 90 minutes. The degree of gelation of each sample was observed, the results of which are set forth in the following Table 6:

TABLE 6

| Sample No. | Material | Endotoxin[1] Concentration ng/ml | Limulus Lysate Assay Reaction |
|---|---|---|---|
| 1 | Polypropylene Bead[2] | 0 | 0 |
| 2 | Endotoxin Standard | 10 | +3 |
| 3 | Endotoxin Standard | 5 | +2 |
| 4 | Endotoxin Standard | 1 | +2 |
| 5 | Sterile Water | 0 | 0 |
| 6 | Polypropylene Bead Endotoxin Standard[3] | 10 | +4 |
| 7 | Perfused Endotoxin Standard | 1 | +1 |

[1]Original concentration of samples before treatment.
[2]Washed polypropylene bead incubated with sterile water.
[3]Polypropylene bead incubated with endotoxin standard.

A comparison of the above results demonstrates the capability of removing Salmonella endotoxin from a biological fluid by contact with polypropylene beads (compare Samples 7 and 4). Additionally, Sample 6 confirms that salmonella endotoxin is absorbed by and tightly bound to the polypropylene bead.

EXAMPLE IX

Several endotoxin standards were prepared from Klebsiella endotoxin obtained from the Food and Drug Administration, Bureau of Biologics, Bethesda, Maryland (reference endotoxin, *Klebsiella pneumonia* carried in saline, Lot 1B). In accordance with instructions provided by the distributor, endotoxin standards were prepared by successive dilutions with pyrogen-free water to provide samples containing 100 ng/ml, 50 ng/ml, 25 ng/ml, 5 ng/ml, and 1 ng/ml endotoxin concentration. A sterile 12 cc syringe was filled with washed polypropylene beads and 3 ml of the 50 ng/ml endotoxin standard was perfused. 0.1 cc of this perfused sample as well as 0.1 cc aliquots of each endotoxin standard sample and the sterile water employed for dilutions were then incubated with 0.1 cc aliquots for the Limulus lysate for 90 minutes at 37° C. and degree of gelation observed in accordance with the aforementioned Limulus lysate assay technique. The results were as follows:

TABLE 7

| Sample No. | Material | Endotoxin[1] Concentration ng/ml | Limulus Lysate Assay Reaction |
|---|---|---|---|
| 1 | Endotoxin Standard | 50 | +3 |
| 2 | Endotoxin Standard | 5 | +3 |
| 3 | Endotoxin Standard | 1 | +1 |
| 4 | Sterile Water | 0 | 0 |
| 5 | Endotoxin Standard | | |

TABLE 7-continued

| Sample No. | Material | Endotoxin[1] Concentration ng/ml | Limulus Lysate Assay Reaction |
|---|---|---|---|
| | after Perfusion | 50 | +2 |

[1]Concentration before treatment and/or assay.

The results of Table 7 confirm the process is capable of removing Klebsiella derived endotoxin. A comparison of treated Sample 5 with the untreated Samples 1–3 shows approximately 80 to 90% of the endotoxin present in the treated standard was removed.

EXAMPLE X

The endotoxin employed in this Example was derived from *Pseudomonas aeruginosa*, prepared by James Jorgensen, Ph. D., Microbiology Department, University of Texas Medical Center, San Antonio, Texas. The endotoxin was prepared from a Verder and Evans group IV Serotype 1369 Pseudomonas employing the Westphal-phenol-water extract technique, a conventional technique for preparing purified endotoxin. The endotoxin was successively diluted with sterile (pyrogen-free) water and separated to provide several endotoxin standard samples containing 10 ng/ml, 5 ng/ml, 2.5 ng/ml, 1 ng/ml, and 0.5 ng/ml endotoxin concentration. 3 ml of a sample of 5 ng/ml endotoxin standard solution was perfused through a sterile syringe containing washed polypropylene beads, described in Example VIII, and the filtrate collected. The Limulus lysate assay was then performed on several of the endotoxin standards and the filtrate from the bead column as described in Example VIII. The results are set forth in the following Table 8:

TABLE 8

| Sample No. | Material | Endotoxin[1] Concentration ng/ml | Limulus Lysate Assay Reaction |
|---|---|---|---|
| 1 | Endotoxin Standard | 10 | +4 |
| 2 | Endotoxin Standard | 5 | +3 |
| 3 | Endotoxin Standard | 1 | +2 |
| 4 | Pyrogen-Free Water | 0 | 0 |
| 5 | Perfused Endotoxin Standard (Filtrate) | 5 | 0 |

[1]Original concentration before treatment and/or assay.

The results of Table 8 demonstrate the capability of removing Pseudomonas endotoxin by this process.

EXAMPLE XI

In this Example, endotoxin derived from all available serotypes of Pseudomonas was employed (Pseudomonas Heptavalent Vaccine Lot #X 41667, containing 0.85 mg/ml of total lipopolysaccharide (endotoxin) and 0.01% Methiolate, Parke Davis & Co., Detroit, Michigan). The endotoxin was diluted in pyrogen-free water in the conventional manner to provide endotoxin standards containing 100 ng/ml, 10 ng/ml, 5 ng/ml, and 1 ng/ml endotoxin concentrations. One polypropylene bead (Shell Polypropylene 5820, Shell Chemical Company, supra) was placed in a test tube containing 0.2 ml of the 100 ng/ml endotoxin standard and incubated for 20 minutes at room temperature. As a control, another polypropylene bead (supra) was placed in a test tube containing the pyrogen-free water employed for dilution of the endotoxin and incubated for the same time period at the same temperature. The respective beads were then washed in pyrogen-free saline, added to 0.1 cc aliquots of Limulus lysate and assayed for endotoxin reaction as described in Example VIII. Several of the endotoxin standards were also assayed with the Limulus lysate. The results are set forth in the following Table 9:

TABLE 9

| Sample No. | Material | Endotoxin[1] Concentration ng/ml | Limulus Lysate Assay Reaction |
|---|---|---|---|
| 1 | Endotoxin Standard | 100 | +4 |
| 2 | Endotoxin Standard | 10 | +2 |
| 3 | Endotoxin Standard | 1 | +1 |
| 4 | Pyrogen-Free Water | 0 | 0 |
| 5 | Polypropylene Bead (in water) | 0 | 0 |
| 6 | Polypropylene Bead (in endotoxin standard) | 100 | +4 |

[1]Original concentration before treatment and/or assay.

The results set forth in Table 9 illustrate the affinity of the polypropylene bead for pseudomonas endotoxin and that the endotoxin is tightly bound thereto, giving a high Limulus lysate assay reaction even after being washed.

EXAMPLE XII

Several porous membrane filters were prepared to determine their effectiveness in removing endotoxin. Four different types of porous membrane materials were employed including: a microporous polypropylene film (CELGARD ® 2500, Celanese Plastics Company); a microporous polyethylene film (CELGARD ® K-801, supra); and two different types of porous membranes of a mixture of cellulose acetate and cellulose nitrate which differ only in effective pore size (Millipore Type GS and Millipore Type HA, Millipore Corp.). Some of the properties of these membranes include the following:

| Property | CELGARD ® 2500[1] | CELGARD ® K-801[1] | MILLIPORE GS[2] | MILLIPORE HA[2] | UNITS |
|---|---|---|---|---|---|
| Polymer or Resin | Hydrophobic Homopolymer Polypropylene | Hydrophobic Homopolymer Polyethylene | Cellulose Acetate-Cellulose Nitrate | Cellulose Acetate-Cellulose Nitrate | |
| Effective Pore Size | 0.04 | 0.50 | 0.22 | 0.45 | Micrometers |
| Porosity | 45 | 65 | 80 | 80 | % |
| Nominal Thickness | 1 (mil) | 2 (mils) | 125 | 125 | Micrometers |

[1]Celanese Plastics Company, Greer, S.C.
[2]Millipore Corp., Bedford, Mass.

The filters were prepared by housing each of the above porous membranes in a stainless steel 25 mm diameter filter housing (Part No. XX3002500, Millipore Corp.). Each filter and its membrane was then flushed with 10 cc of absolute ethyl alcohol followed with 20 cc of pyrogen-free saline.

Two endotoxin standard solutions were prepared from *E. coli* (Difco, E. coli 0111:B4) and *Salmonella typhosa* (Difco, S. typhosa 0901) and respectively diluted with distilled pyrogen-free water in accordance with the previously mentioned dilution technique to provide several endotoxin standards having final concentrations of 50 ng/ml, 5 ng/ml and 0.1 ng/ml endotoxin. With separate 35 ml syringes 20 ml of both endotoxin standard solutions (50 ng/ml endotoxin concentration, respectively) were passed under slight positive pressure through the filters housing each of the above types of porous membranes. Two filters of each type of membrane were used, i.e. one for the *E. coli* endotoxin standard and another for the *S. typhosa* endotoxin standard. Each of the filtrates was collected in a 20 ml polystyrene test tube, respectively. The filtrates and endotoxin standard solutions at varying endotoxin concentrations, used as controls, were then assayed for endotoxin using the Limulus lysate assay technique previously described in Example VIII. The Limulus lysate employed in the assay was obtained from Associates of Cape Cod, Inc., Wood Hole, Mass., which was prepared by the chloroform extraction technique described in "Factors Affecting The Sensitivity Of Limulus Lysate", J. D. Sullivan and S. W. Watson, *Journal Of Applied Microbiology*, Vol. 28, No. 6, pp. 1023-26 (1974). The results are set forth in the following Table 10:

TABLE 10

| Test No. | Membrane[1] Employed | Limulus Lysate S. Typhosa | Assay Reaction E. Coli |
|---|---|---|---|
| 1 | CELGARD ® K-801[2] | 0 | 0 - +1 |
| 2 | CELGARD ® 2500[3] | 0 - +1 | 0 - +1 |
| 3 | MILLIPORE GS[4] | +4 | +4 |
| 4 | MILLIPORE HA[5] | +4 | +4 |
| 5 | Endotoxin Control (50 ng/ml)[6] | +4 | +4 |
| 6 | Endotoxin Control (5 ng/ml)[6] | +4 | +4 |
| 7 | Endotoxin Control (0.1 ng/ml)[6] | +1 | +1 |

[1] Except for controls, endotoxin solutions had original concentrations of 50 ng/ml endotoxin before treatment. Filtrates assayed.
[2] Microporous polyethylene film; 0.50 micrometer pore size. Celanese Plastics Co.
[3] Microporous polypropylene film; 0.04 micrometer pore size. Celanese Plastics Co.
[4] Microporous cellulose acetate - cellulose nitrate film; 0.22 micrometer pore size. Millipore Corp.
[5] Microporous cellulose acetate - cellulose nitrate film; 0.45 micrometer pore size. Millipore Corp.
[6] Endotoxin concentration before assay.

The results of the above Table 10 illustrate the effectiveness of microporous polyethylene and polypropylene films in removing endotoxin from a solution when employed in accordance with the process of the invention. Test Nos. 1 and 2 show that the respective microporous polypropylene and polyethylene films removed essentially all endotoxin from both endotoxin standard solutions tested (*S. typhosa and E. coli*). Further, a comparison of Tests 1 and 2 to Tests 3 and 4 demonstrates that the endotoxins present in the solutions treated were not removed by physical filtration. The pore sizes of Millipore HA and CELGARD ® K-801 are comparable, yet the filtrate in Test 4 as well as that of Test 3 (Millipore GS) gave strong +4 assay reactions, confirming the endotoxin passed through these membranes.

Obviously, many modifications and variations of the invention as hereinbefore set forth may be made without departing from the spirit and scope thereof, and, therefore, only such limitations should be imposed as are indicated in the appended claims.

I claim:

1. A process for selectively removing endotoxin derived from gram-negative bacilli from biological fluids, said process comprising:
    passing a biological fluid contaminated with gram-negative bacilli derived endotoxin through a microporous film, having an effective pore size of from about 0.04 to about 0.5 micrometers, of a non-ionogenic hydrophobic non-polar aliphatic synthetic plastic polymer selected from the group consisting of a substantially crystalline, non-polar aliphatic hydrocarbon thermoplastic polymer, a substantially crystalline non-polar aliphatic thermoplastic fluorocarbon polymer, a cross-linked aliphatic silicone elastomeric polymer and mixtures thereof, whereby the endotoxin is adsorbed onto the surface of the polymer; and
    removing the biological fluid from contact with said polymer essentially free of said endotoxin.

2. The process of claim 1 wherein the microporous film is a microporous polypropylene film having an effective pore size of about 0.04 micrometers and a porosity of about 45%.

3. The process of claim 1 wherein the microporous film is a microporous polyethylene film having an effective pore size of about 0.50 micrometers and a porosity of about 65%.

* * * * *

UNITED STATES PATENT AND TRADEMARK OFFICE
CERTIFICATE OF CORRECTION

PATENT NO. : 4,059,512
DATED : November 22, 1977
INVENTOR(S) : Nick S. Harris

It is certified that error appears in the above-identified patent and that said Letters Patent are hereby corrected as shown below:

[73] Assignee: "Preventative Systems, Inc." should read --Preventive Systems, Inc. , Galveston, Texas --.

Signed and Sealed this

Eighteenth Day of April 1978

[SEAL]

Attest:

RUTH C. MASON
*Attesting Officer*

LUTRELLE F. PARKER
*Acting Commissioner of Patents and Trademarks*